United States Patent [19]

Tsutsui et al.

[11] Patent Number: 5,132,998
[45] Date of Patent: Jul. 21, 1992

[54] RADIOGRAPHIC IMAGE PROCESSING METHOD AND PHOTOGRAPHIC IMAGING APPARATUS THEREFOR

[75] Inventors: Hiroshi Tsutsui, Yawata; Koichi Ohmori, Toyonaka; Tetsuro Ohtsuchi, Osaka; Sueki Baba, Suita, all of Japan

[73] Assignee: Matsushita Electric Industrial Co., Ltd., Osaka, Japan

[21] Appl. No.: 486,854

[22] Filed: Mar. 1, 1990

[30] Foreign Application Priority Data

Mar. 3, 1989 [JP] Japan .................. 1-052288

[51] Int. Cl.⁵ ............................. G01B 15/02
[52] U.S. Cl. ............................ 378/99; 378/56; 378/62
[58] Field of Search .......... 378/45, 82, 83, 87, 378/88, 90, 46, 48, 49, 56, 89, 207, 53, 62, 99, 6, 44; 358/111

[56] References Cited

U.S. PATENT DOCUMENTS

| | | | |
|---|---|---|---|
| 3,757,122 | 9/1973 | Bossen et al. | 378/56 |
| 3,996,471 | 12/1976 | Fletcher et al. | 250/498 |
| 4,037,104 | 7/1977 | Allport | 378/56 |
| 4,599,514 | 7/1986 | Cho | 378/53 |
| 4,686,695 | 8/1987 | Macovski | 378/146 |

OTHER PUBLICATIONS

Nuclear Instruments & Methods in Physics Research, Section -a vol. 242, No. 3, Jan. 1986, Amsterdam pp. 596-602; F. P. Bolin et al.: "A dual beam study with isotopic X- and Gamma-rays for in vivo limph pool assay".

Journal of Testing and Evaluation. vol. 13, No. 3, May 1985, Philadelphai U.S. pp. 211-216; F. L. Roder: "Principles, history, and status of Dual-Energy computerized tomographic explosives detection".

Physics in Medecine and Biology. vol. 23, No. 6, Nov. 1978, London GB pp. 1101-1114; H. W. Kramer et al.: "Combined cortical thickness and bone density determination by Photon absorptiometry".

*Primary Examiner*—Janice A. Howell
*Assistant Examiner*—Don Wong
*Attorney, Agent, or Firm*—Stevens, Davis, Miller & Mosher

[57] ABSTRACT

Transmission images are obtained by radiating X-rays having two different energy levels onto a subject in one direction, and then transformed into logarithmic images, respectively. From these logarithmic images, a contrast ratio due to the two kinds of X-rays having different energies is obtained. From this contrast ratio, the term relating to the thickness of the subject is eliminated, thereby providing information only relating to the quality of the material. By collating the information with the previously measured data of materials, the material of the subject is identified.

22 Claims, 5 Drawing Sheets

F I G. 4
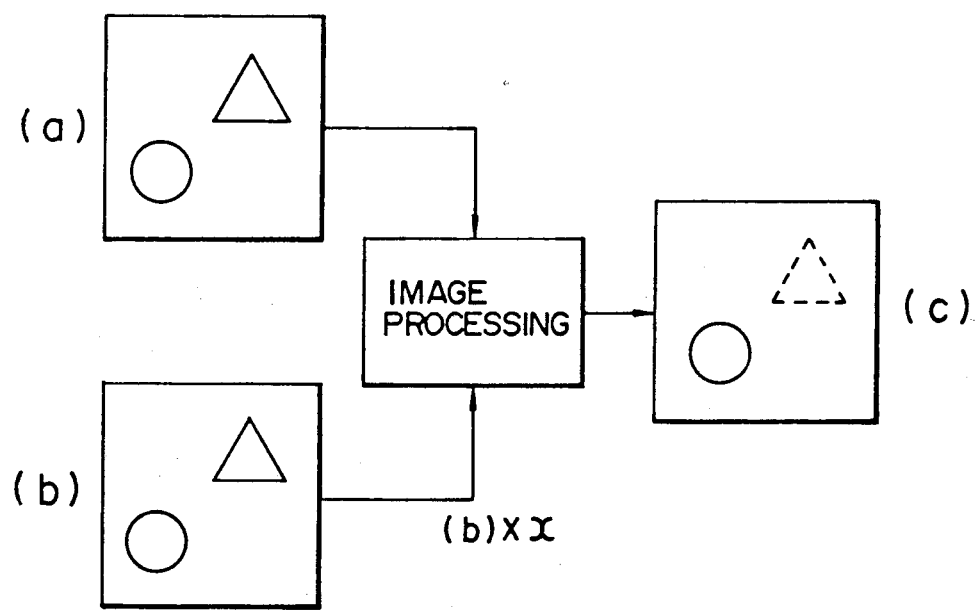

RADIOGRAPHIC IMAGE PROCESSING METHOD AND PHOTOGRAPHIC IMAGING APPARATUS THEREFOR

BACKGROUND OF THE INVENTION

The present invention relates to an image processing method and a photographing apparatus therefor used in an apparatus for industrial analysis or a medical diagnostic apparatus.

PRIOR ART INVENTION

A transmission image produced by a radiographic ray which is radiated onto a subject in one direction is basically composed of the a product of absorption coefficient and thickness. The basic principle of the radioactive ray transmission will be described below. A radioactive ray transmitting or penetrating through a subject has a characteristic expressed by the following equation:

$$I(E) = I_o(E)/exp\{\mu(E) \cdot X\}$$

where

E is a specific energy of a radioactive ray
$I_o(E)$ is an incident intensity of the radioactive ray
$I(E)$ is a transmission intensity of the radioactive ray
X is thickness of a subject.

As shown in the above equation, the transmission intensity varies according to $\mu(E)$ and X. This means that a transmission radioactive ray image necessarily contains information relating to the thickness of the subject.

Since a transmission image necessarily contains information relating to the thickness of the subject, the image simply gives a shaded shape.

SUMMARY OF THE INVENTION

Radiation having more than two different kinds of energy levels are radiated on a subject in the same direction for radiography, thereby producing transmission images. Then, logarithmic images are prepared through logarithmic transformation of the transmission images of different energy levels. Then a contrast ratio of the subject in the logarithmic images is measured. Alternatively, one of the logarithmic images is multiplied by a suitable coefficient, and a subtraction is conducted between both images. Thus, the coefficient value at which a specific part of the subject is eliminated can be obtained.

By measuring the contrast ratio of the logarithmic images as mentioned above, the information relating to the thickness of the subject is eliminated and the information relating only to the atomic number and the kind of the material can be obtained.

BRIEF DESCRIPTION OF THE DRAWINGS

FIG. 4 shows an example of image processing.

DETAILED DESCRIPTION OF THE EMBODIMENTS

Figure 1:
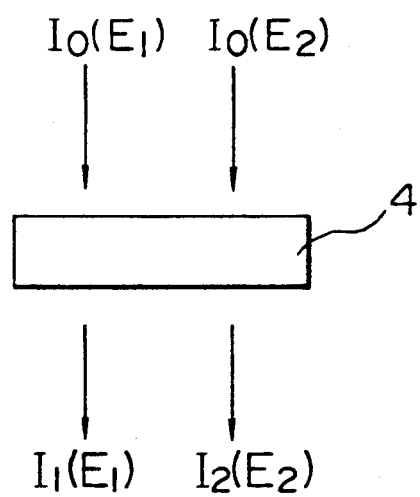
FIG. 1 is an illustration showing the basic principle of a radiation transmission.

Referring to FIG. 1, the basic principle of the present invention will be described below.

The contrast of images transmitted through the subject are expressed as follows:

$$I_1(E_1) = I_o(E_1)/exp\{-\mu(E_1) \cdot X\} \quad (1)$$

$$I_2(E_2) = I_o(E_2)/exp\{-\mu(E_2) \cdot X\} \quad (2)$$

where $E_1$, $E_2$ are different energies of radiations,
$I_o(E_1)$, $I_o(E_2)$ are intensities of the incident radiations, and
$I_1(E_1)$, $I_2(E_2)$ are intensities of the radiations transmitted through the subject These images are transformed into logarithmic images as follows, where a natural logarithmic transformation is used:

$$Ln\, I_1(E_1) = Ln\, I_o(E_1)\{-\mu(E_1) \cdot X\} \quad (3)$$

$$Ln\, I_2(E_2) = Ln\, I_o(E_2)\{-\mu(E_2) \cdot X\} \quad (4)$$

The image contrasts of the subject in these logarithmic transformations are expressed as follows, corresponding to energy levels $E_1$ and $E_2$:

$$Ln\, I_o(E_1) - Ln\, I_1(E_1) = \{\mu(E_1) \cdot X\} \quad (5)$$

$$Ln\, I_o(E_2) - Ln\, I_2(E_2) = \{\mu(E_2) \cdot X\} \quad (6)$$

The contrast ratio of the subject is deduced from the equations (5) and (6) as follows:

$$\text{Contrast ratio of the subject} = \mu(E_1)/\mu(E_2) \quad (7)$$

As understood from the equation (7), by using the contrast ratio of the subject, the information relating to the thickness of the subject can be eliminated. In other words, the physical properties of the subject can be expressed as parameters. If absorption coefficients of various elements and materials are known in advance, the elements and materials forming the subject can be specified based on the contrast ratio of the subject.

Further, in case the elements and materials forming the subject are limited or specified, the composition ratio of the elements and materials can be obtained based on the contrast ratio of the subject.

When radioisotopes (abbreviated as RI) are used as incident radiation sources having energies of $E_1$ and $E_2$, RI can be selected from those listed in Table 1.

TABLE 1

| KIND OF RI | ENERGY (KeV) |
| --- | --- |
| $^{129}I$ | 39.6 |
| $^{241}Am$ | 59.5 |
| $^{129}Cd$ | 88.0 |
| $^{153}Gd$ | 97.4, 103.2 |
| $^{57}Co$ | 122.1, 136.5 |

Figure 2:
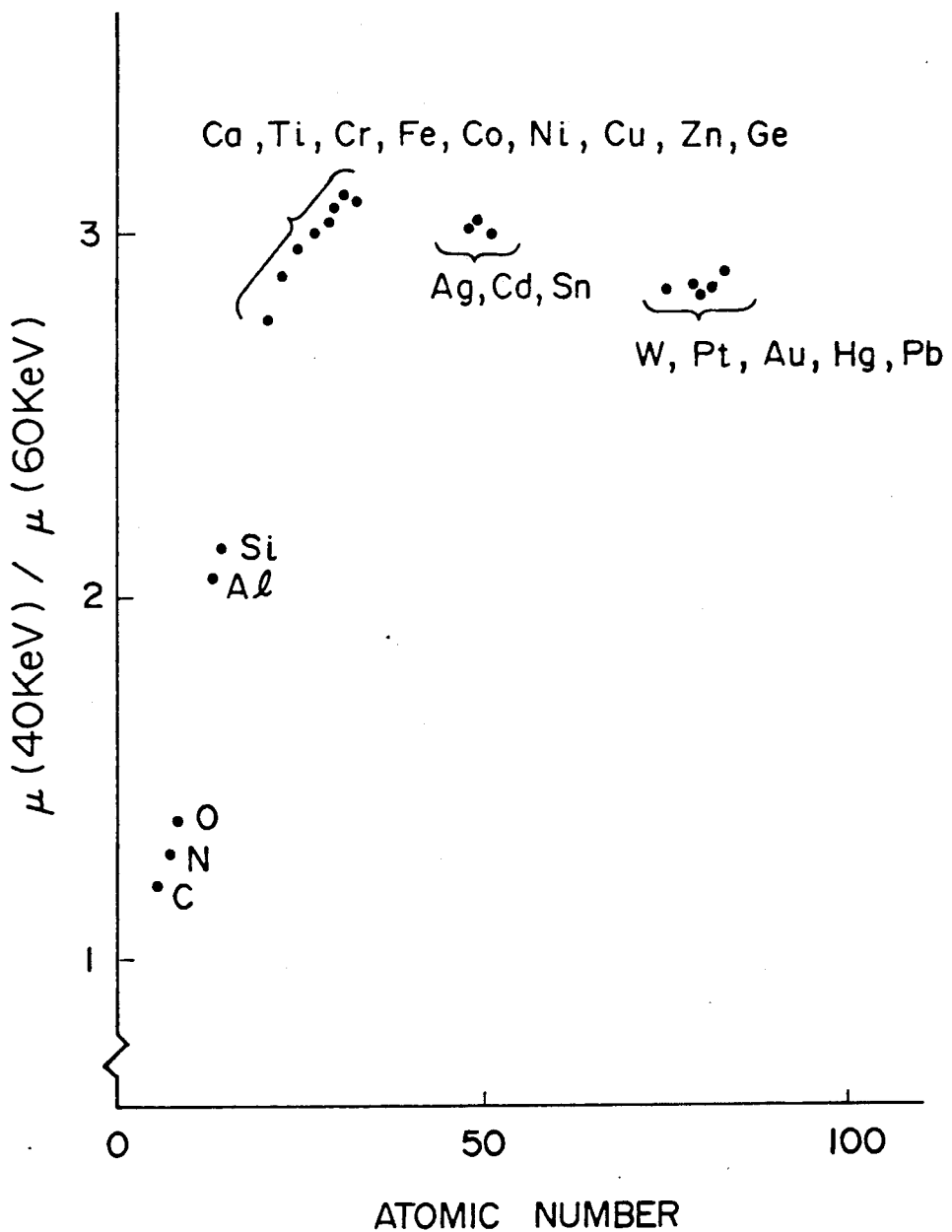
FIGS. 2 and 3 are illustrations showing correlations between atomic number and contrast ratio of the images.

As an example, $^{129}I$ and $^{241}Am$ were selected among those listed in Table 1, and various subjects were radiated by these radiations of different energy levels. The contrast ratios of the various materials, which were obtained through logarithmic transformation of the transmission images, are shown in FIG. 2. As seen in FIG. 2, the contrast ratios for elements having smaller atomic numbers such as C, O or N distribute in a range 1 to 1.4, those for elements Al or Si in a range near 2, and those for elements having atomic numbers greater than that of Ti in a range 2.8 to 3.2. In case the atomic number is smaller than 20, the contrast ratio and the atomic number fall in a proportionate relationship to each other, and the elements and the materials can be identified based on the contrast ratios. Roughly speaking, in case the contrast ratio is smaller in comparison with that of Al, which is selected as a reference body, it is determined that the subject is a resin mainly composed of C, while in case the contrast ratio is greater, the subject is a metal.

Figure 3:
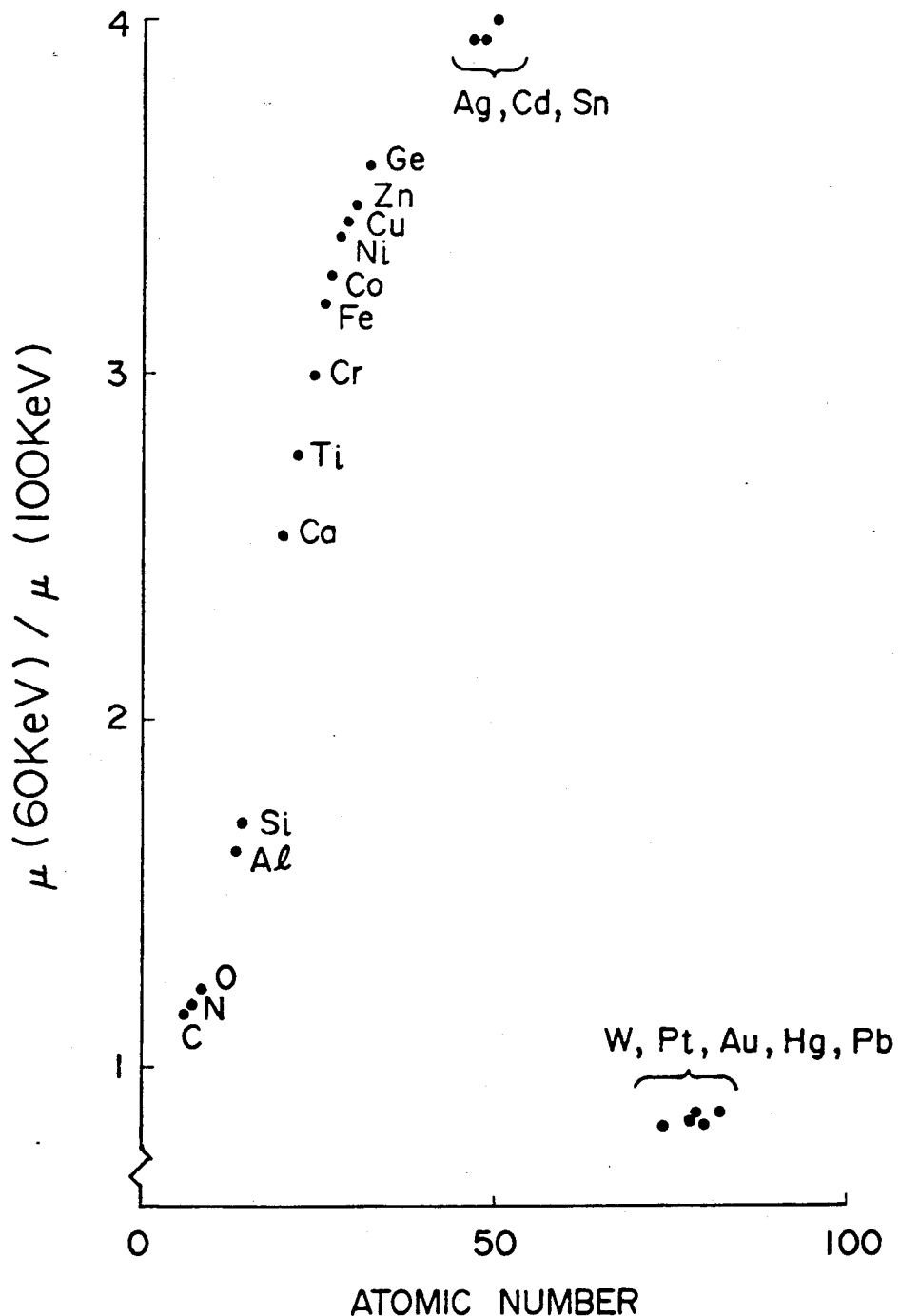

As another example, $^{241}$Am and $^{152}$Gd were used, and the contrast ratios in the logarithmic images transformed from the transmission images are shown in FIG. 3. In this case, since the energy levels were changed, the above-mentioned proportionate relationship was maintained for the materials having atomic number smaller than 50. As a result, the range where the elements or materials can be identified was widened in comparison with the above-mentioned example.

$^{109}$Cd and $^{57}$Co have the same function when combined with the other RI.

In case an X-ray source is used as a radiation source, the energy spectrum (radiation quality) varies depending on the X-ray generating method, the kind of X-ray tube, and the electric voltage to be applied. Further, as the thickness of the subject increases, the energy spectrum (radiation quality) of the X-ray having transmitted through the subject varies. Therefore, it is necessary to previously find out contrast ratios with respect to various materials having final thickness by using a specific X-ray source. As a method for changing the X-ray energy level, there is a method where the voltage applied to the X-ray tube is changed. If a metal such as Cu is used as a filter, the separation of the energies is significantly improved.

As mentioned above, the X-ray effective energy can be changed by changing the voltage to be applied in combination with a metal filter, and the changing of the X-ray effective energy produces the same result as in the case of using RI. The effective energy in a range 10 KeV to 140 KeV is effectively used for materials having an atomic number smaller than 20, while the effective energy in a range 40 to 200 KeV is effectively used for materials having an atomic number greater than 20.

In the above, a method utilizing a contrast ratio has been described. Here, a simpler image processing method will be described. Two logarithmic images transformed from transmission images of a subject obtained by use of two different energies are prepared. One of the logarithmic images is multiplied by a coefficient, and a subtraction is conducted between the two images. In this step, if the coefficient is equal to the above-mentioned contrast ratio, the figure of the subject is eliminated from the image obtained by the subtraction. In other words, the image after the subtraction is investigated with respect to the elimination behavior of each part of the subject figure while changing the value of the coefficient, and the coefficient value obtained at the eliminated part can be regarded as the contrast ratio of that part.

FIG. 4 shows the outline of the above-mentioned image processing. Two transmission images are prepared by using two kinds of energies. These transmission images are transformed into logarithmic images (a), (b) by applying a logarithmic transformation on the transmission images. One image (b) of the logarithmic images (a), (b) is multiplied by a coefficient X, and a subtraction is conducted between these logarithmic images. The image (c) obtained through the subtraction is investigated while changing the coefficient X. For example, in FIG. 4, the coefficient value is read out just when the triangular figure of the subject eliminates from the image. This coefficient corresponds to the contrast ratio of the triangular figure, and can identify the quality of the material of the triangular figure.

Further, by arranging a reference body such as Al near to the subject and normalizing the contrast ratio by using the contrast ratio of the reference body, it becomes easy to identify the kind of the element and material.

Figure 5:
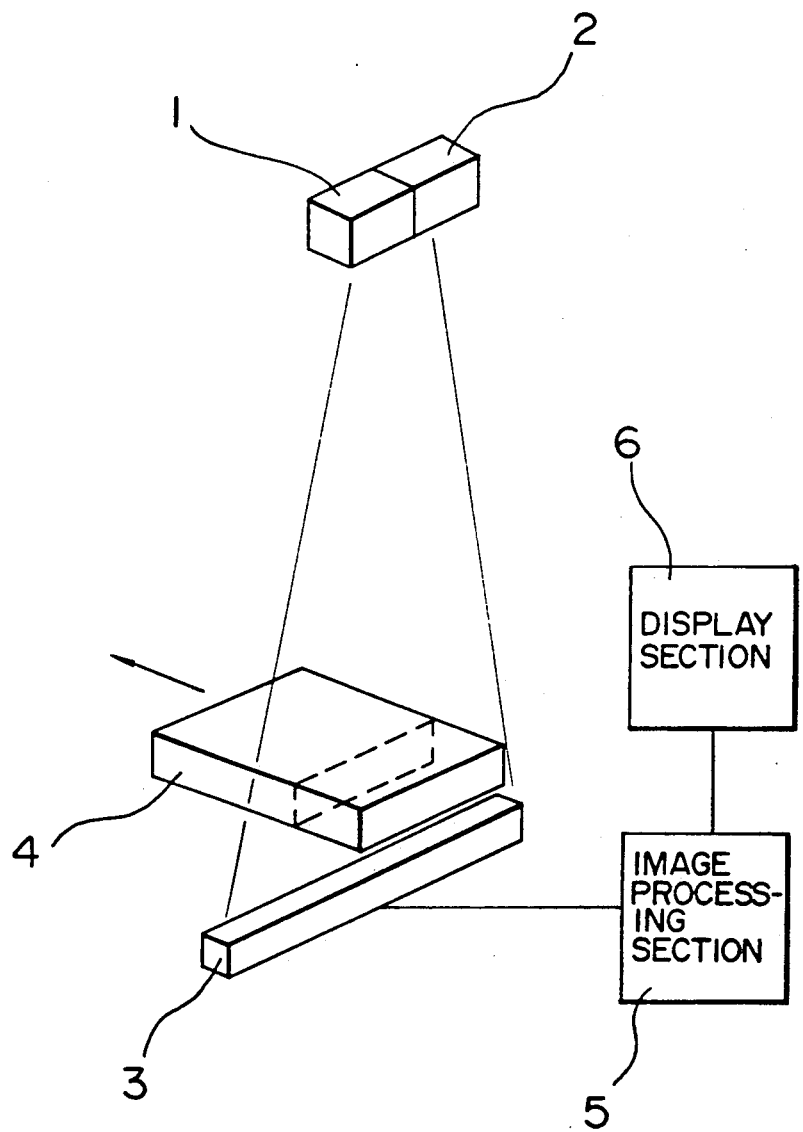
FIG. 5 shows an example of radiographic imaging apparatus.

FIG. 5 shows a radiographic imaging apparatus in an embodiment form according to the present invention. RI ray sources (1), (2) having different energy levels and a radiation sensor (3) having a line-like shape are provided, and a subject (4) is moved in a direction indicated by the arrow, thereby producing a transmission image of the subject. As the radiation sensor, a semiconductor sensor composed of such as Si, Ge, GaAs, CdIe, or HgI can be selected and used. As for the radiographic imaging method, there are two methods, namely a method in which two steps of radiographic imagings are required and each radiographic imaging is conducted by using one radiation source, and another method in which two radiation sources are used at the same time, and the output pulses from the semiconductor radiation sensor are discriminated with respect to the pulse height, thereby producing transmission images of different energy levels at the same time. By using the pulse height discrimination, in case of using an X-ray as a radiation source, transmission images of different energy levels can be obtained without requiring change in the electric voltage or use of a metal filter. The transmission images thus obtained are subjected to a logarithmic transformation under the function of an image processing section 5, and then, the contrast ratio is obtained and indicated on an indicating section 6.

As a radiation sensor usable in the present invention, a two-dimensional sensor or an area sensor such as a plate coated with a photo-stimulable phosphor having a nice linearity of sensitivity or an image-intensifier can be used.

According to the present invention, by radiographic images obtained by use of radiations having different energy levels, preparing logarithmic images through a logarithmic transformation of the transmission images, and finding the contrast ratio of the subject, it is possible to identify the elements or materials of the subject and to analyze the composition ratios.

What we claim is:

1. A radiographic image processing method, comprising steps of:
    obtaining information relating to transmission images which are obtained by radiating radiations having more than two different energy levels onto a subject in the same direction,
    preparing a logarithmic image through a logarithmic transformation of the transmission image obtained by use of a radiation of an energy level, and another logarithmic image through a logarithmic transformation of another transmission image obtained by use of a radiation of another energy level, and obtaining an image contrast ratio of the logarithmic images at a specific part of the subject by use of said logarithmic images.

2. A radiographic image processing method claimed in claim 1, further comprising steps of obtaining, in advance, ratios of absorption coefficients defined for two specific energy levels with respect to various elements and materials, collating said ratios of the absorption coefficients with image contrast ratios at the specific part of the subject, and identifying the elements or materials at said specific part or obtaining the composition ratio of the same part.

3. A radiographic image processing method claimed in claim 1, further comprising steps of normalizing said ratios of the absorption coefficients of various elements and materials by using a reference ratio of absorption coefficients of a specific element defined for two specific energy levels, collating said normalized absorption coefficient ratios with the image contrast of a specific part of the subject, and identifying the elements or materials at said specific part or obtaining the composition ratio of the same part.

4. A radiographic image processing method claimed in claim 1, further comprising steps of disposing a reference body composed of a special element or material in the subject, and collating the image contrast ratios of the reference body obtained by use of two kinds of energies with the image contrast ratio of a specific part of the subject, and identifying the elements or materials at said specific part or obtaining the composition ratio at the same part.

5. A radiographic image processing method claimed in claim 1, further comprising steps of obtaining logarithmic images through logarithmic transformation of transmission images of a typical element or material which are to be analyzed by use of $\gamma$-ray or X-ray sources having various energy levels, obtaining, in advance, reference image contrast ratios of the logarithmic images which are obtained by use of two specific kinds of energies, collating said reference image contrast ratios with the image contrast ratio of a specific part of the subject in the logarithmic images obtained by use of two kinds of energies, and identifying the elements or materials at said specific part or obtaining the composition ratio at the same part.

6. A radiographic image processing method claimed in claim 1, further comprising steps of preparing image contrast ratios of logarithmic images transformed from the transmission images obtained by applying two kinds of energies on aluminum (Al) which serves as a reference body, collating said image contrast ratio of Al with the image contrast ratio of a specific part of the subject in the logarithmic images obtained by use of two kinds of energies, and identifying the elements or materials at said specific part or obtaining the composition ratio at the same part.

7. A radiographic image processing method claimed in claim 1, wherein, for identifying an element having an atomic number smaller than 20 or a compound material having an effective atomic number smaller than 20, radioactive rays having energies in a range 10 KeV to 140 KeV are used.

8. A radiographic image processing method claimed in claim 1, wherein, for identifying an element having an atomic number greater than 20 or a compound material having an effective atomic number greater than 20, radioactive rays having energies in a range 40 KeV to 200 KeV are used.

9. A radiographic image processing method claimed in claim 1, further comprising steps of multiplying one of the ologarithmic images transformed from the transmission images of the subject obtained by use of two different energies by a coefficient, obtaining a difference between the logarithmic image multiplied by a coefficient and the other logarithmic image, continuously changing the coefficient value for obtaining a coefficient value at which a specific part of the subject is eliminated form the image, and identifying three elements or materials at said specific part or obtaining the composition ratio at the same part based on said coefficient value.

10. A radiographic image processing method claimed in claim 1, further comprising steps of obtaining, in advance, ratios of absorption coefficients defined for two special energy levels with respect to various elements, collating said ratios of the absorption coefficients with the coefficient value at which a specific part of the subject is eliminated from the image, and identifying the elements or materials at said specific part or obtaining the composition ratio at the same part.

11. A radiographic image processing method claimed in claim 2, further comprising steps of normallizing the ratios of the absorption coefficients of various elements and materials by using a reference ratio of absorption coefficients of a specific element defined for two special energy levels, collating said normalized absorption coefficient ratio with the coefficient value at which a specific part of the subject is eliminated form the image, and identifying the elements or materials at said specified pat or obtaining the composition ratio at the same part.

12. A radiographic image processing method claimed in claim 1, further comprising steps of disposing a reference body composed of a specific element or material in the subject, collating the image contrast ratio of the reference body obtained by use of two kinds of energies with the coefficient value at which a specific part of the subject vanishes from the image, and identifying the elements or materials at said specific part or obtaining the composition ratio at the same part.

13. A radiographic image processing method as in claim 1, further comprising the steps of:

normalizing ratios of the absorption coefficients of various elements and materials by using a reference ratio of absorption coefficients of a specific element defined for two specific energy levels, collating said normalized absorption coefficient ratios with the image contrast of a specific part of the subject, and identifying the elements or materials at said specific part or obtaining the composition ratio of the same part.

14. A radiographic image processing method as in claim 2, further comprising the steps of:

disposing a reference body composed of a special element or material in the subject, and collating the image contrast ratios of the reference body obtained by use of two kinds of energies with the image contrast ratio of a specific part of the subject, and identifying the elements or materials at said specific part or obtaining the composition ratio at the same part.

15. A radiographic image processing method as in claim 4, further comprising the steps of:

obtaining, in advance, ratios of absorption coefficients defined for two special energy levels with respect to various elements, collating said ratios of the absorption coefficients with the coefficient value at which a specific part of the subject is eliminated from the image, and identifying the elements or materials at said specific part or obtaining the composition ratio at the same part.

16. A radiographic image processing method as in claim 1, further comprising the steps of:

normalizing ratios of the absorption coefficients of various elements and materials by using a reference ratio of absorption coefficients of a specific element defined for two special energy levels, collating said normalized absorption coefficient ratio with the coefficient value at which a specific part of the subject is eliminated from the image, and identifying the elements or materials at said specified part or obtaining the composition ratio at the same part.

17. A radiographic imaging apparatus for radiographic images including radiation sources, detecting means for detecting radiation, image processing means, indicating means, and means for determining the image contrast ratio of a subject based on logarithmic images transformed from the transmission images which are obtained by use of radioactive rays having different energy levels.

18. A radiographic imaging apparatus for radioactive ray images claimed in claim 17, wherein, as a radioactive ray source, $^{57}Co$, $^{109}Cd$, $^{129}I$, $^{153}Gd$, $^{241}Am$ are selected among radioisotopes capable of radiating rays, and one of said radioisotopes or more than two of said radioisotopes are used in combination.

19. A radiographic imaging apparatus for radiographic images claimed in claim 17, wherein, as a radiation source, X-ray is used, and the effective energy of the X-ray is controlled by changing the voltage applied on an X-ray generator in combination with the use of a metal filter.

20. A radiographic imaging apparatus for radiographic images claimed in claim 17, wherein, as a radiation detecting means, a panel coated with a photostimulable phosphor is used.

21. A radiographic imaging apparatus for radiographic images claimed in claim 17, wherein, as a radiation detecting means, an image-intensifier is used.

22. A radiographic imaging apparatus for radiographic images claimed in claim 17, wherein, as a radiation detecting means, a semiconductor detector selected from a group consisting of Si, Ge, GaAs, CdTe and HgI is used.

* * * * *